United States Patent
Horrobin et al.

(10) Patent No.: US 6,630,157 B1
(45) Date of Patent: Oct. 7, 2003

(54) THERAPEUTIC AND DIETARY COMPOSITIONS CONTAINING ESSENTIAL FATTY ACIDS AND BIOACTIVE DISULPHIDES

(75) Inventors: David F. Horrobin, Stirling (GB); Hans-Jurgen Tritschler, Bad Homberg (DE)

(73) Assignee: Viatris GmbH & Co. KG. (DE)

( * ) Notice: Subject to any disclaimer, the term of this patent is extended or adjusted under 35 U.S.C. 154(b) by 0 days.

(21) Appl. No.: 09/463,300

(22) PCT Filed: Jul. 22, 1998

(86) PCT No.: PCT/GB98/02155

§ 371 (c)(1),
(2), (4) Date: Aug. 15, 2000

(87) PCT Pub. No.: WO99/04782

PCT Pub. Date: Feb. 4, 1999

(30) Foreign Application Priority Data

Jul. 22, 1997 (GB) .............................................. 9715444

(51) Int. Cl.⁷ .............................................. A61K 47/00
(52) U.S. Cl. ..................... 424/439; 424/464; 424/484; 424/489; 514/724; 514/866
(58) Field of Search ................................ 424/439, 464, 424/484, 489; 514/866, 724

(56) References Cited

U.S. PATENT DOCUMENTS

| | | | |
|---|---|---|---|
| 5,043,328 A | 8/1991 | Weithmann | |
| 5,084,481 A | 1/1992 | Ulrich et al. | |
| 5,380,920 A | 1/1995 | Paust et al. | |
| 5,472,698 A | * 12/1995 | Rawlings et al. | ........... 424/401 |
| 5,489,694 A | 2/1996 | Paust et al. | |
| 5,532,269 A | 7/1996 | Koltringer | |
| 5,569,670 A | 10/1996 | Weischer et al. | |
| 5,602,183 A | 2/1997 | Martin et al. | |
| 6,048,846 A | * 4/2000 | Cochran | ...................... 514/168 |
| 6,063,820 A | * 5/2000 | Cavazza | ...................... 514/739 |

FOREIGN PATENT DOCUMENTS

| | | |
|---|---|---|
| EP | 0 218 460 A2 | 4/1987 |
| EP | 0 232 501 A1 | 8/1987 |
| EP | 0 244 832 A2 | 11/1987 |
| EP | 0 292 870 A2 | 11/1988 |
| WO | WO 96/34846 | 11/1996 |
| WO | WO 96/34855 | 11/1996 |

OTHER PUBLICATIONS

Packer et al, "Antioxidant Properties of Lipoic Acid", pp. 545–590.
McCarty et al, "Medical Hypotheses", pp. 139–151, 1984.
Merck, "Aklomide", pp. 33, 1989.
Cameron et al, "Effects of α–lipoic acid on neurovascular function in diabetic rats: Interaction with essential fatty acids", Diabetologia (1998) 41 pp. 390–399.
"Pschyrembel Klinisches Worterbuch" XP002050663 1990.
Das UN, "Essential fatty acid metabolism in patients . . . ", Prostaglandins Leukot Essent Fatty Acids 52(6) Jun. 1995 pp. 387–391.

* cited by examiner

*Primary Examiner*—Thurman K. Page
*Assistant Examiner*—Charesse Evans
(74) *Attorney, Agent, or Firm*—Nixon & Vanderhye P.C.

(57) ABSTRACT

Compostions of GLA and/or other EFAs with TA or related compounds, and their use in therapy or nutrition or in preparation of composition for therapy or nutrition, especially to improve cell membrane EFA concentration and/or (particularly in diabetic complications) impaired nerve function and blood flow.

25 Claims, 2 Drawing Sheets

FIG. 1

Figure 1:
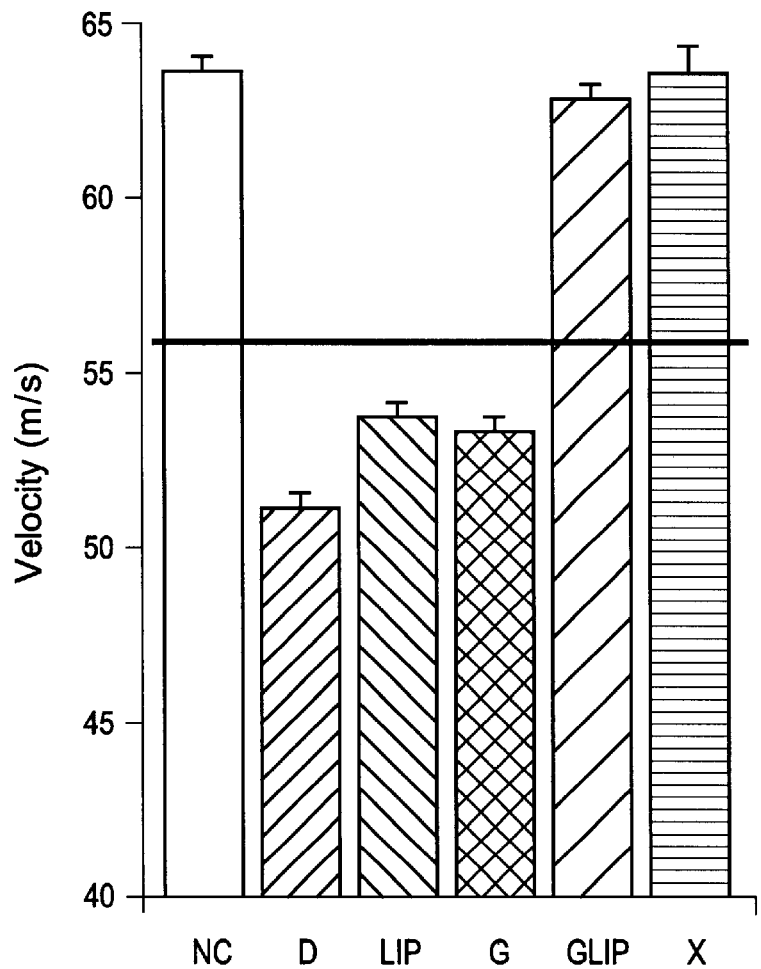

NC = normal control animals
D = Diabetic animals, untreated
LIP = D + 20 mg/kg/day alpha-lipoic acid
G = D + 20 mg/kg/day gamma-linolenic acid
X = D + 48 mg/kg/day of a 1, 3 propane diol containing the equivalent of 23.4 mg/kg/d gamma-linolenic acid and 18.1 mg/kg/d alpha lipoic acid NC = normal control animals D = Diabetic animals, untreated LIP = D + 20 mg/kg/day alpha-lipoic acid G = D + 20 mg/kg/day gamma-linolenic acid X = D + 48 mg/kg/day of a 1, 3 propane diol containing the equivalent of 23.4 mg/kg/d gamma-linolenic acid and 18.1 mg/kg/d alpha lipoic acid

Nutritive perfusion

Blood flow increases without change in blood pressure indicating an increase in vascular conductance caused by vasodilation.
Groups as in Figure 1.

THERAPEUTIC AND DIETARY COMPOSITIONS CONTAINING ESSENTIAL FATTY ACIDS AND BIOACTIVE DISULPHIDES

FIELD

The invention relates to therapeutic and dietary compositions.

FATTY ACIDS

Gamma-linolenic acid (GLA), its immediate metabolite dihomogamma-linolenic acid, (DGLA) and, in certain circumstances, the DGLA metabolite arachidonic acid (AA), have wide ranges of desirable biological effects as essential nutrients and as nutrients or therapeutic agents specific preventative or therapeutic effects in various diseases including those of the skin (such as eczema and psoriasis), those of metabolism (in particular diabetes and its complications such as retinopathy, neuropathy, nephropathy and cardiovascular problems), those of inflammation and autoimmunity (such as rheumatoid arthritis, osieoarthritis, Sjogren's syndrome, systemic lupus, Crohn's disease, ulcerative colitis), those of the respiratory system (including asthma, pulmonary hypertension and pulmonary fibroses), those of the psyche and central nervous system (such as schizophrenia, dementia of Alzheimer and vascular or other types, depression and multiple sclerosis), those of the cardiovascular system (such as hypertension and coronary and peripheral arterial disease), those of the kidney (such as glomerulonephritis and other inflammatory and autiommuune conditions), those of the gastrointestinal system (such as oesophagitis, gastritis, peptic ulcer, Crohn's disease and ulcerative colitis) and those of the endocrine system and its target organs (such as benign breast disease and benign prostatic disease). Cancer and pre-cancerous conditions may also respond to treatment with GLA and DGLA. GLA and DGLA have also been found to be beneficial in animal diseases and also in the care of diseased and of normal skin where they improve skin blood flow and skin smoothness.

Other essential fatty acids, of the n-3 series, notably stearidonic acid (SA), eicosapentaenoic acid (EPA), docosapentaenoic acid (DPA) and docosahexaenoic acid (DHA) also have many desirable nutritional and therapeutic effects, and many of the prior patents filed by the present applicants, relate to use of either or both series of essential fatty acids in various condition EPA 0 218 460, concerning the complications of diabetes being one example.

Both series of essential fatty acids are well known in themselves and their terminology and relations are set out below

TABLE 1

| n-6 EFA's | | n-3 EFA's |
| --- | --- | --- |
| 18:2n-6 (Linoleic acid, LA) | | 18:n-3 (α-Linolenic acid, ALA) |
| ↓ | delta-6-desaturase | ↓ |
| 18:3n-6 (γ-Linolenic acid GLA) | | 18:4n-3 (Stearidonic acid) |
| ↓ | elongation | ↓ |
| 20:3n-6 (Dihomo-γ-linolenic acid, DGLA) | | 20:4n-3 |
| ↓ | delta-5-desaturase | |
| 20:4n-6 (Arachidonic acid, AA) | | 20:5n-3 (Eicosapentaenoic acid, EPA) |
| ↓ | elongation | ↓ |
| 22:4n-6 (Adrenic acid, AdrA) | | 22:5n-3 |
| ↓ | delta-4-desaturase | ↓ |
| 22:5n-6 | | 22:6n-3 (Docosahexaenoic acid, DHA) |

The acids, which in nature are of the all—cis configuration, arc systematically named as derivatives of the corresponding octadecanoic, cicosanoic or docosanoic acids, e.g. z,z-octadeca-9,12 -dienoic acid or z,z,z,z,z,z-docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2 n-6 or 22.6 n-3, are convenient. Initials, e.g. EPA, and shortened forms of the name e.g. eicosapentaenoic acid, are used as trivial names in some instances. Further the acids beyond the 6desaturation step are informally known as the "6-desaturated" acids.

DISULPHIDES

Quite different types of chemical entity are α-lipoic acid, also known as thioctic acid (TA), and related compounds. In the body TA is converted to dihydrolipoic acid (DHL) during the formation of acetyl-CoA from pyruvic acid or the formation of succinyl-CoA from α-oxoglutaric acid, and during other oxido-reduction reactions. DHL can be converted back to TA by lipoic acid dehydrogenase, which requires the co-factor AND. TA and DHL have been seen as equivalent since they are rapidly interconverted in the body. The structures are:

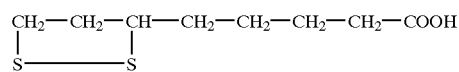

Thiotic acid or α-lipoic acid
(TA)

with R, S and racemic forms and

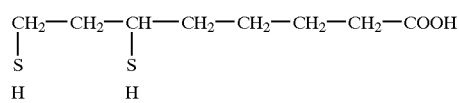

Dihydrolipoic acid (DHL)

also with R, S and racemic forms. In the context of this application thioctic acid means isomerically pure D- or S-alpha-lipoic acid, racemic alpha-lipoic acid or any mixture of the R- and S- isomers, and correspondingly for compounds related to thioctic acid including the reduced forms.

TA and the related free disulphide compounds, which are strongly lipophilic, are antioxidant agents capable of forming a redox couple in the body and they have for example been found to be of therapeutic value in the management of complications of diabetes, especially diabetic neuropathy Such complications are believed to be associated with excessive rates of oxidation of lipids and proteins and the TA/DHL redox couple has been seen as significant in neutralising many species of free radicals. Furthermore it can "recycle" other important antioxidants such as α-tocopherol and ascorbate and bring about an increase of intracellular glutathione. In addition to diabetic complications, there is evidence that TA can enhance sensitivity to insulins so being of value in the pre-diabetic syndrome X and in obesity.

Metabolites of TA with similar function to TA are tetranorlipoic acid (TALA), bisnorlipoic acid (BALA) and 8-hydroxy-bisnorlipoic acid (8BALA) with R and S isomers as a with lipoic acid.

The antioxidant properties and consequent previously proposed clinical applications of α-lipoic acid and its reduced form in diabetes and other conditions are discussed in the Handbook of Antioxidants (eds. E Cadanas and L Packer, Marcel Dekkar, New York 1996) see Chapter 18 pages 545–591, by Packer Witt and Tritschler Further, the applicants' prior patent application PCT GB 96/01053 (WO 96/34846) discloses fatty acid/antioxidant derivatives of 1,3-propane diol and their use in conditions which antioxidants are beneficial including cardiovascular diseases, cancer and inflammatory disorders. Particular diesters disclosed are of GLA or DHA and lipoic acid. Related compounds, formally derivatives of dihydroxy methane, are disclosed in the applicants' further specification PCT GB 96/01052 (WO 96/34855). In those applications it is however emphasised that compounds containing moieties of the fatty acid and lipoic acid are used: there is no reference to the co-administration of fatty acids and lipoic acid as separate molecules nor for particular purposes. In Hoechst U.S. Pat. No. 5,043,328 lipoic acid is mentioned as an antioxidant though in a prostaglandin-metabolism context, on gastrointestinal problems and skin and subdermal tissue malfunctions.

NEW WORK DONE INVENTION

Available therapies in treatment and prevention of most of the conditions mentioned so far, including diabetes, insulin resistance, syndrome X, and diabetic complications such as neuropathy and retinopathy, are far from satisfactory It seemed to us that the use of the above two different approaches simultaneously might be worth testing in relation to diabetic complications. GLA is believed to work mainly on the micro-circulation whereas TA/DHL is believed to work mainly on oxidation mechanisms, but it seemed reasonable to see whether the co-application of these agents might have at least additive effects.

Figure 2:
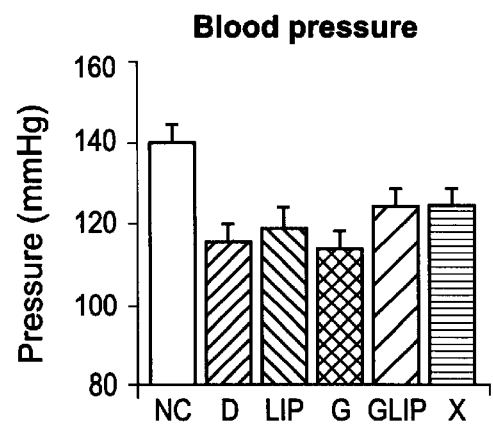
Figure 2:
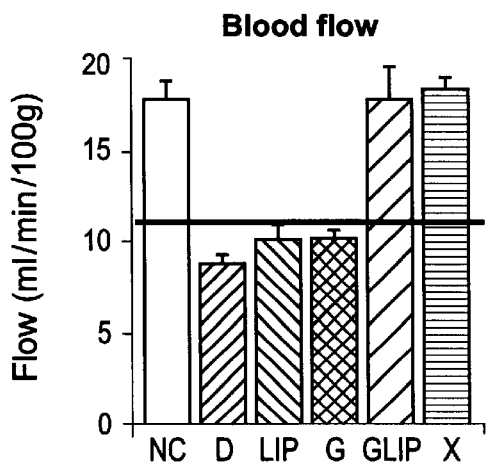
Figure 2:
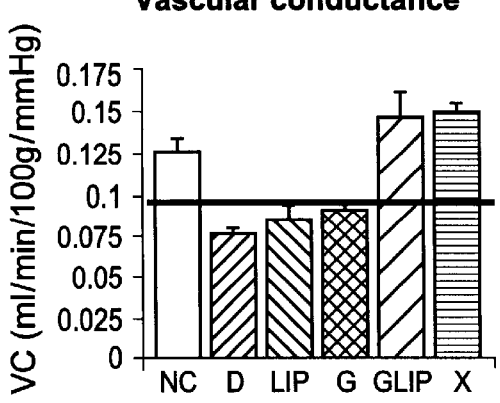

In fact in measurements of nerve conduction velocity and nerve blood flow a dramatic and unexpected synergism was observed, with the effect of the two agents applied together being far greater than the sum of the effects of the two agents when applied alone. The results are shown in FIGS. 1 and 2. In diabetic animals both nerve conduction and nerve blood is flow are considerably affected. Both can be completely normalised by the co-administration of amounts of GLA and TA that have little effect alone.

The results with EFA's and their synergistic effects with TA were completely unexpected and we decided to investigate them further. Vitamin E, like TA, is a lipophilic antioxidant and is one which is generally regarded as being physiologically more important than TA. However, when vitamin E was administered together with GLA in animals with diabetes there was no enhancement at all of the effect of GLA. Equally, in several clinical studies we have shown that the effects of GLA in conditions like atopic eczema, breast pain, rheumatoid arthritis and cardiovascular disease are not enhanced by the co-administration of vitamin E. There was therefore no reason at all to suspect the dramatic potentiation we have observed, which we do not think can be explained by the antioxidant effect.

In an effort to explore the effect further, we have performed preliminary experiments on rats on the effects of the administration of either GLA, EPA or DHA with or without the so anti-oxidants vitamin E, vitamin C or TA. Each fatty acid was added to the food at 0.1% by weight for a period of two weeks. The diet also contained either no other added material (control) or 0.1% by weight of vitamin E, vitamin C or TA. After two weeks the animals were killed and the levels of the fatty acids or their immediate metabolites determined in plasma phospholipids and in red cell membrane phospholipids. Neither vitamin E nor vitamin C had any effects on the levels of the fatty acids in either plasma or red cells. We can therefore conclude that there is no effect of anti-oxidants per se on the metabolism of the GLA, EPA or DHA in this situation. Equally, there were no effects of TA on the plasma phospholipid fatty acid composition. In contrast, in each of the groups the concentrations of the relevant fatty acids in red cell phospholipids were increased by 10–20%. This demonstrates that TA has a thitherto unknown and unsuspected effect on the incorporation of EFAs into cell membranes. This effect does not appear to be related to antioxidant activity.

What we are showing is that TA can enhance the incorporation of EFAs into cell membrane phospholipids. This will have effects on membrane structure and on the availability of the EFAs for cell signalling systems and is likely to account for the synergistic effects we have observed on nerve function and nerve blood flow in the diabetic animals. The effect is a general one which is applicable to all EFAs and not just to GLA.

The invention broadly concerns compositions of GLA and/or other EFAs, with the TA or related compounds, and their use in therapy or nutrition or in preparation of compositions to for therapy or nutrition. The conditions concerned are set out herein but especially the invention is concerned to improve cell membrane EFA concentration and/or, particularly in diabetic complications specifically, impaired nerve function (for example motor nerve conduction velocity) and blood flow Impaired blood flow may also be important it other illnesses, especially disorders of the heart and peripheral circulation. Impaired EPA incorporation into membranes may be an important problem, in most of the conditions listed.

PARTICULAR STATEMENT OF INVENTION

In particular the invention provides:
1. Use in the manufacture of a medicament for treatment to improve or maintain cell membrane EFA concentration in health or any of the conditions set out herein, or use in such treatment itself, of an essential fatty acid, particularly one beyond the 6desaturation step in the n-6 and n-3 metabolic pathways, and a bioactive disulphide, particularly TA or a related compound, including the use of one active where for co-administration with the other and each active being present as such or as a derivative releasing the active in the body.
2. Use in the manufacture of a medicamnent for therapy (including prophylaxis of impaired nerve function for example motor-nerve conduction velocity) or blood flow in any of the conditions set out herein but particularly in diabetic neuropathy, retinopathy, nephorpathy or other complications of diabetes, or use in such therapy itself, of an essential fatty acid, particularly one beyond the 6desaturation step in the n-6 and n-3 metabolic pathways, and a biocompatible disulphide, particularly TA or a related compound, including the use of one active where for co-administration with the other and each active being present as such or as a derivative releasing the active in the body.

3. Use as above, the actives comprising at least one of GLA, DGLA and AA, and/or SA EPA, DPA and DHA.

4. Use as above, the actives comprising one or more of TA, TALA, BALA or 8-BALA as such or in respective reduced form.

5. Use as above the actives further comprising one or more other essential nutrients particularly vitamins A, D and E; B group vitamins such as riboflavin pyridozine niacin or niacinamide; folic acid, vitamin C; or assimilable zinc chromium magnesium or selenium.

6. Use as above the fatty acid and the disulphide being presented for administration of 1 mg to 100 g/day of each preferably 10 mg to 10 g/day very preferably 50 mg to 5 g/day and in a weight ratio of 1:20 to 20:1 more preferably 1:5 to 5:1 very preferably 1:3 to 3:1.

7. Use as above, in the context of the treatment management or prevention of any of the conditions referred to herein and in particular but without restriction in:

a) diabetes and its complications particularly diabetic retinopathy, all forms of insulin resistance and syndrome X, related conditions such as obesity, diabetic neuropathy, diabetic retinopathy, diabetic nephropathy, diabetic macrovascular coronary and peripheral arterial disease, diabetic leg ulcers and diabetic impotence.

b) disorders in which reduced blood flow to any tissue is important, particularly insulin resistance, type II diabetes, and coronary peripheral or cerebral vascular disease of any actiology.

c) any inflammatory disorder particularly rheumatoid arthritis, osteoarthritis and asthma.

d) any psychiatric or central nervous system disorder particularly schizophrenia, depression, ischameic dementas, Alzheimer's disease, other dementias, multiple sclerosis, and attention deficit hyperactivity disorder e) eczema and psoriasis.

f) any respiratory disorder particularly asthma, pulmonary hypertension and pulmonary fibrosis.

g) any cardiovascular disorder particularly hypertension, coronary or peripheral arterial disease or thrombotic disorder.

h) Crohn's disease or ulcerative colitis i) any endocrine disorder, particularly benign breast and prostaic diseases.

j) any form of cancer or pre-cancerous condition, including cachexia associated with cancer.

k) improvement of athletic performance, for example, by increasing muscle blood flow and the utilisation of energy in humans or in animals.

As noted above the most effective EFAs are the 6desaturated EFAs particularly GLA, AA, DGLA, SA, EPA, DPA or DHA suitably in a dose range of 1 mg to 100 g, preferably 10 mg to 10 g and very preferably 50 mg to 5 g per day. The disulphides, such as TA, BALA, TAL and 8BALA or their reduced forms may be used in similar dose ranges. The weight ratio of the EFA to disulphide may for example be from 1:20 to 20:1 but is preferably from 1:5 to 5:1, more preferably from 1:3 to 3:1. The EFAs and the disulphide may, further, each be used in any appropriate combined chemical form that is pharmacologically acceptable and capable of raising the concentration of the EFA or the disulphide related compound in blood or other bodily tissues. Such prongs may include triglycerides, phospholipids, other glycerides, propane diol derivatives, germinal diols and others known to those skilled in the art. The EFA and the disulphide may even be combined in the same molecule, whose function is then to act as a pro-drug for both the EFA and the disulphide. Examples are 1,3-propane diol derivatives made as disclosed in our PCT application GB 96/01053 (WO 20 96/34836) and germinal diol derivatives made as disclosed in our PCT application GB 96/01052 (WO 96/34855).

The actives may be presented together or separately with instructions stating how they are to be administered. When presented in separate dosage forms the two may be provided together in packs. They may be presented for example by oral, eternal, parenteral, topical, rectal, or vaginal routes using formulations known to those experienced in the arm The actives may also be provided in nutritional supplements, medical foods, functional foods, nutraceuticals or ordinary foods together with other essential nutrients including minerals and vitamins such as vitamins A, D and E; B group vitamins such as riboflavin, pyridoxine, niacin or nicotinamide; folic acid; vitamin C; or assimilable zinc, chromium, magnesium or selenium. Such nutrients may be provided in any appropriate bioassimilable chemical form.

EXPERIMENTAL

Initial experimental evidence was obtained by studying rats made diabetic by the administration of streptozotocin. In such animal, complications resembling human complications of diabetes develop, and are characterised by reduction in conduction velocity to of impulses along the sciatic nerve and reduction in blood flow to the sciatic nerve. The reduction in blood flow is particularly important and is likely to be relevant to many complications of diabetes including retinopathy, nephropathy macrovascular arterial disease of the heart and peripheral arteries, impotence and leg ulceration. It may also be relevant to many of the other conditions in which essential fatty acids are useful treatments, including the inflammatory disorders.

Five groups of animals given streptozotocin (STZ) were tested. They were accepted into the study only if they developed unequivocal elevation of blood glucose after the STZ. Ten animals acted as normal controls.

Ten animals were diabetic but untreated. Eight animals were treated with TA alone. 11 with GLA alone and 11 with combined TA and GLA. The GLA was added to the food to give an approximate dose of 20 mg/kg/daily and TA was given by daily intraperitoneal injection at a dose of 20 mg/kg/day. Because fats are metabolised in relation to the surface area, and because the surface area/volume ratio is much higher in a small animal than in a large one, these doses are very approximately equivalent to a dose of around 2–3 mg/kg/daily in an adult human.

The animals were made diabetic by injection of 45 mg kg STZ intraperitoneally. Rats were males of the Sprague Dawley strain and were 19 weeks old at the time of STZ injection. The animals were left for 6 weeks after the STZ to allow the nerve damage to develop and were then given treatment with nothing or with GLA or TA or both together for 2 weeks At the end of the two weeks, the animals were anaesthetised and the motor nerve conduction velocity measured in the perineal branch of the sciatic nerve. Sciatic nerve blood flow was also measured by microelectrode polarography hydrogen clearance Figures for the motor nerve conduction velocity and the total nerve blood flow were plotted. The TA alone and the GLA alone both produced small improvements in nerve conduction velocity and in nerve blood flow but the improvements at these doses were far from restoration of normality. Estimated additive effects of the two compounds added to together were also far from restorative of normality. However, and in contrast to an expected additive effect, the two compounds together effectively normalised both nerve conduction velocity and nerve blood flow. Based on previous dose/response studies of GLA alone or ALA alone, the presence of GLA or of TA appeared to amplify the effect of the other compound around ten-fold. It contrasts with an absence of effect on nerve conduction with TA alone referred to in Packer et al (loc. cit., pages 570–572).

The above illustrates the invention in terms of treatment, as actual disease conditions may be addressed by administration of the compounds. In terms of medicaments and their preparation the invention is illustrated in the following examples:

EXAMPLES

The following are examples of compositions effective in relation to the complications of diabetes, and other purposes, set out.

1. Soft or hard gelatin capsules, each containing 100 mg of TA, TALA, BALA or 8-BALA as such or in respective reduced form, with 100 mg of GLA, DGLA, AA, SA, EPA, DPA or DHA, to be used in a dose of 1 to 4 capsules per day.
2. Capsules as in 1 but in which the daily dose of the active ingredients ranges from 0 mg to 200 mg for the thioctic acid related compound and from 20 mg to 200 mg for the fatty acid.
3. Capsules as in 1 or 2 but in which the fatty acid is provided as a derivative, namely an ethyl or other ester; a mono, di or triglyceride; a phospholipid; an amide or any other derivative which gives rise to the biologically active fatty acid in the body.
4. Capsules as in 1 or 2, containing a diester with a residue of a fatty acid selected from GLA, DGLA, AA, SA, EPA, DPA and DHA, and a residue of thioctic acid or one of the related compounds TALA, BALA or 8-BALA as such or in respective reduced form, the diester being of 1,3-propane diol prepared as described in Example S or 17 of WO 96134846 or of dihydroxymethane prepared as described in Example 4 of WO 96/34855, reference to which specifications may be made.
5. Tablets or capsules each containing 50, 100 or 200 mg of TA, TALA, BALA or 8-BALA as such or in respective reduced form, presented in the same pack, for example in blister packing, as soft or hard gelatin capsules each containing 50 mg. 100 mg or 200 mg of LA, DGLA, AA, SA, EPA, DPA or DHA, each dosage form taken at a dose of 1–4 units/day.
6. A nutritional supplement for use in humans or animals with diabetes or any other disease which provides in each capsule 50 mg of TA, 100 mg of GLA or DGLA, 100 mg of DHA, 50 mg of ascorbic acid, the recommended daily allowances of the B group vitamins and 300 mg of chromium as the picolinate.
7. A functional food for use by people with diabetes or any other disease which in addition to calories and essential nutrients provides in each portion 100 mg of GLA and 100 mg of TA. optionally also with DGLA, AA, SA, EPA, DPA or DHA.
8. A skin care or cosmetic preparation for eczema or psoriasis in which 0.1% to 2.0% of TA and 0.1% to 10.0% of GLA or DGLA are incorporated into an emollient base.
9. A food or drink for use by athletes or people in exercise training for any reason, including rehabilitation after injury, heart disease or stroke, which in each portion provides 50–200 mg of TA and 50–200 mg of GLA or DGLA optionally with other essential nutrients and fatty acids.
10. A food, drink or supplement for use by horses or dogs which provides 1–50 mg/kg/day of TA together with 1–50 mg/kg/day or GLA or DGLA optionally with other essential nutrients and fatty acids.

What is claimed is:

1. A method of treating complications of diabetes, comprising administering to a patient an effective amount of an essential fatty acid selected from the group consisting of GLA, DGLA, AA, SA, EPA, DPA and DHA and a biocompatible disulphide selected from the group consisting of TA, TALA, BALA and 8-BALA or its respective reduced form, and optionally administering at least one of vitamin A, vitamin D vitamin E, a B-group vitamin, vitamin C, or an assimilable zinc, chromium, or selenium.

2. A method of treating complications of diabetes, comprising administering to a patient an effective amount of an essential fatty acid and a biocompatible disulphide, each being present as such or in a form releasing the essential fatty acid or the disulphide in the patient's body.

3. The method of claim 2, wherein the essential fatty acid is beyond the 6-desaturation step in the n-6 and n-3 metabolic pathways.

4. The method of claim 2, wherein the biocompatible disulphide is thiotic acid.

5. The method of claim 3, wherein the essential fatty acid is at least one of GLA, DGLA, AA, SA, EPA, DPA and DHA.

6. The method of claim 2, wherein the biocompatible disulphide is at least one of TA, TALA, BALA and 8-BALA or its respective reduced form.

7. The method of claim 2, further administering at least one of vitamin A, vitamin D, vitamin E, a B-group vitamin, vitamin C, or an assimilable zinc, chromium, magnesium or selenium.

8. The method of claim 2, wherein the essential fatty acid and the biocompatible disulphide are each administered in amounts of from 1 mg to 100 gram per day.

9. The method of claim 8, wherein the essential fatty acid and the biocompatible disulphide are each administered in amounts of from 10 mg to 10 gram per day.

10. The method of claim 9, wherein the essential fatty acid and the biocompatible disulphide are each administered in amounts of from 50 mg to 5 gram per day.

11. The method of claim 2, wherein the essential fatty acid and the biocompatible disulphide are administered in a weight ratio of 1:20 to 20:1.

12. The method of claim 11, wherein the essential fatty acid and the biocompatible disulphide are administered in a weight ratio of 1:5 to 5:1.

13. The method of claim 12, wherein the essential fatty acid and the biocompatible disulphide are administered in a weight ratio of 1:3 to 3:1.

14. A method of treating complications of diabetes, comprising administering to a patient an effective amount of an essential fatty acid and a biocompatible disulphide, each being present as such or in a form releasing the essential fatty acid or the disulfide in the patient's body.

15. The method of claim 14, wherein the essential fatty acid is beyond the 6-desaturation step in the n-6 and n-3 metabolic pathways.

16. The method of claim 14, wherein the biocompatible disulphide is thiotic acid.

17. The method of claim 15, wherein the essential fatty acid is at least one of GLA, DGLA, AA, SA, EPA, DPA and DHA.

18. The method of claim 14, wherein the biocompatible disulphide is at least one of TA, TALA, BALA and 8-BALA or its respective reduced form.

19. The method of claim 14, further administering at least one of vitamin A, vitamin D, vitamin E, a B-group vitamin, vitamin C, or an assimilable zinc, chromium, magnesium or selenium.

20. The method of claim 14, wherein the essential fatty acid and the biocompatible disulphide are each administered in amounts of from 1 mg to 100 gram per day.

21. The method of claim 20, wherein the essential fatty acid and the biocompatible disulphide are each administered in amounts of from 10 mg to 10 gram per day.

22. The method of claim 21, wherein the essential fatty acid and the biocompatible disulphide are each administered in amounts of from 50 mg to 5 gram per day.

23. The method of claim 14, wherein the essential fatty acid and the biocompatible disulphide are administered in a weight ratio of 1:20 to 20:1.

24. The method of claim 23, wherein the essential fatty acid and the biocompatible disulphide are present in a weight ratio of 1:5 to 5:1.

25. The method of claim 24, wherein the essential fatty acid and the biocompatible disulphide are administered in a weight ratio of 1:3 to 3:1.

* * * * *